(12) United States Patent
Elian et al.

(10) Patent No.: US 9,121,885 B2
(45) Date of Patent: Sep. 1, 2015

(54) SENSOR PACKAGE AND METHOD OF MANUFACTURING THEREOF

(75) Inventors: Klaus Elian, Alteglofsheim (DE); Horst Theuss, Wenzenbach (DE); Guenther Ruhl, Regensburg (DE)

(73) Assignee: Infineon Technologies AG, Neubiberg (DE)

(*) Notice: Subject to any disclaimer, the term of this patent is extended or adjusted under 35 U.S.C. 154(b) by 576 days.

(21) Appl. No.: 12/857,242

(22) Filed: Aug. 16, 2010

(65) Prior Publication Data

US 2012/0038352 A1 Feb. 16, 2012

(51) Int. Cl.
*G01N 27/72* (2006.01)
*G01R 33/07* (2006.01)

(52) U.S. Cl.
CPC .............. *G01R 33/072* (2013.01); *G01N 27/72* (2013.01); *Y10T 29/49002* (2015.01)

(58) Field of Classification Search
CPC ...................................... G01R 33/072
USPC ................................. 324/239, 251
See application file for complete search history.

(56) References Cited

U.S. PATENT DOCUMENTS

| | | | | |
|---|---|---|---|---|
| 5,057,774 A * | 10/1991 | Verhelst et al. | ............... | 324/537 |
| 5,074,929 A * | 12/1991 | Bradley et al. | ............... | 148/101 |
| 5,517,104 A * | 5/1996 | Kawakami | ............... | 324/117 R |
| 6,078,172 A * | 6/2000 | Lenhard | ............... | 324/117 R |
| 6,392,422 B1 * | 5/2002 | Kammer et al. | ............... | 324/650 |
| 6,534,707 B1 * | 3/2003 | Bator et al. | ............... | 174/353 |
| 6,538,546 B2 * | 3/2003 | Serino et al. | ............... | 336/96 |
| 6,807,507 B2 * | 10/2004 | Kumar et al. | ............... | 702/124 |
| 6,989,665 B2 * | 1/2006 | Goto | ............... | 324/117 H |
| 7,126,354 B2 * | 10/2006 | Deboy et al. | ............... | 324/713 |
| 7,385,394 B2 * | 6/2008 | Auburger et al. | ............... | 324/252 |
| 7,394,249 B2 * | 7/2008 | Kang et al. | ............... | 324/253 |
| 7,449,801 B2 * | 11/2008 | Bayerer | ............... | 307/135 |
| 7,528,592 B2 * | 5/2009 | Marchand | ............... | 324/117 R |
| 7,612,553 B2 * | 11/2009 | Kinzel | ............... | 324/117 H |
| 7,714,588 B2 * | 5/2010 | Montreuil | ............... | 324/522 |
| 7,716,502 B2 * | 5/2010 | Muresan et al. | ............... | 713/300 |
| 7,990,132 B2 * | 8/2011 | Dupuis et al. | ............... | 324/117 R |
| 8,310,225 B2 * | 11/2012 | Michalak | ............... | 324/117 H |
| 2002/0124934 A1 * | 9/2002 | Koch et al. | ............... | 156/97 |
| 2002/0190831 A1 * | 12/2002 | Hess et al. | ............... | 336/174 |
| 2004/0080307 A1 * | 4/2004 | Ohtsuka | ............... | 324/117 H |
| 2004/0080308 A1 * | 4/2004 | Goto | ............... | 324/117 H |
| 2005/0030018 A1 * | 2/2005 | Shibahara et al. | ............... | 324/251 |
| 2005/0035761 A1 * | 2/2005 | Park et al. | ............... | 324/244 |
| 2005/0072011 A1 * | 4/2005 | Miyashita et al. | ............... | 33/355 R |
| 2006/0175674 A1 * | 8/2006 | Taylor et al. | ............... | 257/421 |
| 2006/0202690 A1 * | 9/2006 | Park et al. | ............... | 324/249 |
| 2006/0220256 A1 * | 10/2006 | Shim et al. | ............... | 257/777 |
| 2006/0226826 A1 * | 10/2006 | Teppan | ............... | 324/117 H |
| 2007/0120552 A1 * | 5/2007 | Kaneda | ............... | 324/117 R |
| 2007/0145972 A1 * | 6/2007 | Auburger et al. | ............... | 324/252 |
| 2007/0279053 A1 * | 12/2007 | Taylor et al. | ............... | 324/252 |
| 2007/0290161 A1 * | 12/2007 | Tokuoka et al. | ............... | 252/62.54 |

(Continued)

*Primary Examiner* — Patrick Assouad
*Assistant Examiner* — Demetrius Pretlow
(74) *Attorney, Agent, or Firm* — Slater & Matsil, L.L.P.

(57) ABSTRACT

A sensor package and a method for manufacturing a sensor package are disclosed. An embodiment includes a sensor and a conductive line, wherein the sensor is arranged proximate to the conductive line. The sensor and the conductive line are isolated and at least partially encapsulated. A soft magnet is arranged in, on or around the encapsulation, wherein the soft magnet includes a composition of an insulating material and a material having soft magnetic properties.

24 Claims, 5 Drawing Sheets

(56) References Cited

U.S. PATENT DOCUMENTS

| | | | |
|---|---|---|---|
| 2008/0002324 A1* | 1/2008 | Logiudice et al. | 361/91.2 |
| 2008/0084201 A1* | 4/2008 | Kojori | 324/117 R |
| 2008/0136399 A1* | 6/2008 | Alfano et al. | 323/301 |
| 2008/0185673 A1* | 8/2008 | Theuss | 257/433 |
| 2008/0202249 A1* | 8/2008 | Yokura et al. | 73/726 |
| 2008/0237818 A1* | 10/2008 | Engel et al. | 257/676 |
| 2009/0009280 A1* | 1/2009 | Ishihara | 336/234 |
| 2009/0040665 A1* | 2/2009 | Elms et al. | 361/42 |
| 2009/0057799 A1* | 3/2009 | Chan et al. | 257/433 |
| 2009/0058412 A1* | 3/2009 | Taylor et al. | 324/252 |
| 2009/0140725 A1* | 6/2009 | Ausserlechner | 324/207.2 |
| 2009/0243595 A1* | 10/2009 | Theuss et al. | 324/207.11 |
| 2009/0295384 A1* | 12/2009 | Teppan | 324/253 |
| 2009/0315536 A1* | 12/2009 | Koch | 324/117 R |
| 2010/0001715 A1* | 1/2010 | Doogue et al. | 324/117 H |
| 2010/0141249 A1* | 6/2010 | Ararao et al. | 324/244 |
| 2010/0276769 A1* | 11/2010 | Theuss et al. | 257/421 |
| 2010/0321032 A1* | 12/2010 | Holce et al. | 324/601 |
| 2011/0297831 A1* | 12/2011 | Yao et al. | 250/338.4 |

* cited by examiner

SENSOR PACKAGE AND METHOD OF MANUFACTURING THEREOF

TECHNICAL FIELD

The present invention relates generally to a sensor package and method for manufacturing a sensor package. The present invention further relates to a system comprising a current sensor.

BACKGROUND

Generally, an electrical current may be measured by using a shunt. A shunt is a resistor of known resistance, which is placed in series with a load so that all of the current to be measured flows through the resistor. The voltage drop across the resistor is proportional to the current flowing through resistor. Since the resistance of the resistor is known, a voltmeter connected across the resistor can display the current value.

One disadvantage of shunts is their high resistance and therefore their loss of energy.

SUMMARY OF THE INVENTION

These and other problems are generally solved or circumvented, and technical advantages are generally achieved, by preferred embodiments of the present invention.

In accordance with an embodiment of the present invention a sensor package is disclosed. A sensor package comprises a conductive line and a sensor, wherein the sensor is arranged proximate to the conductive line. The sensor and the conductive line are electrically isolated and at least partially encapsulated. A soft magnet is arranged in, on and/or around the encapsulation, wherein the soft magnet comprises a composition of an insulating material and a material having soft magnetic properties.

BRIEF DESCRIPTION OF THE DRAWINGS

For a more complete understanding of the present invention, and the advantages thereof, reference is now made to the following descriptions taken in conjunction with the accompanying drawing, in which.

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The present invention will be described with respect to preferred embodiments in a specific context, namely a sensor package. The invention may also be applied to current sensors.

Figure 1:
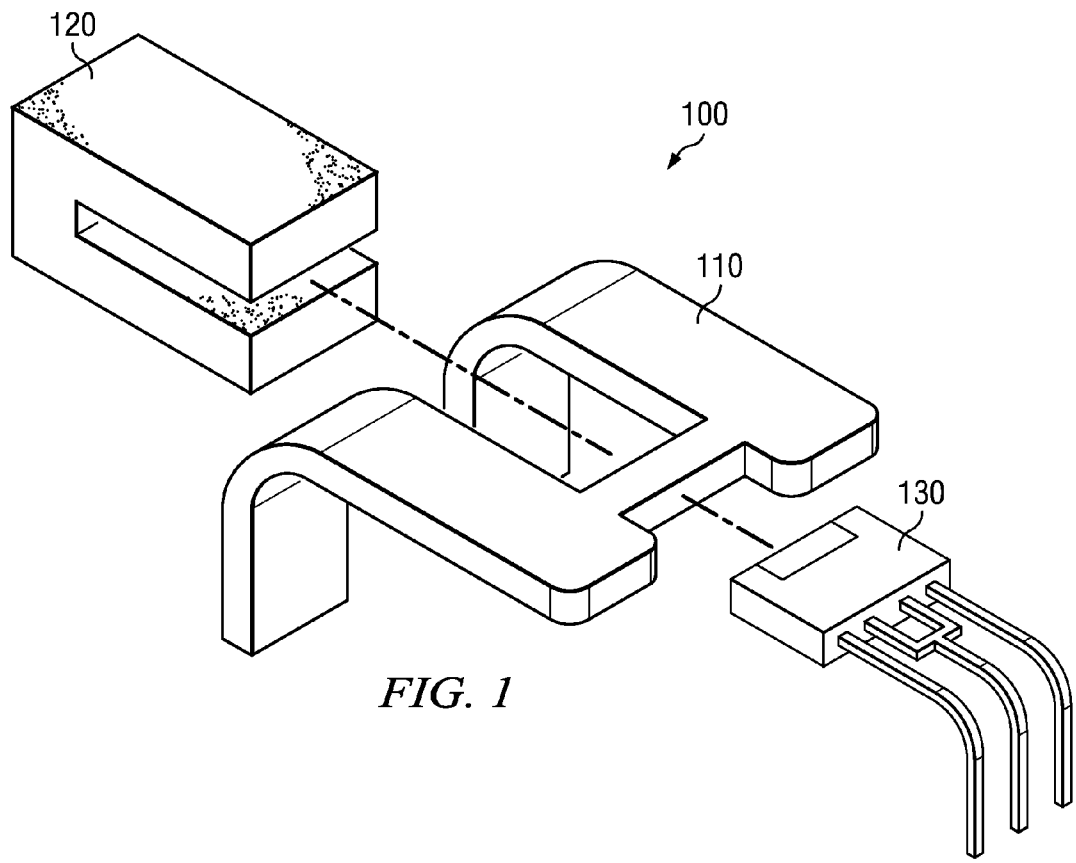
FIG. 1 is an illustration of a conventional arrangement of a current rail and a packaged magnetic sensor not yet finally assembled.
Figure 2:
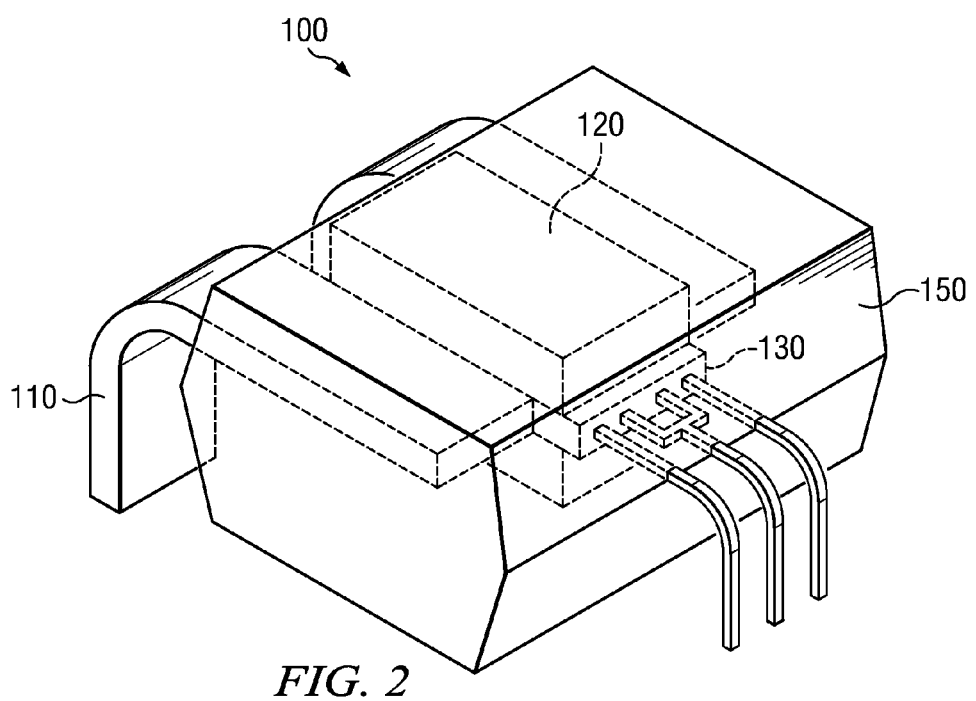
FIG. 2 is an illustration of a conventional current sensor package.

FIG. 1 shows elements typically integrated into a conventional current sensor package 100. The conventional current sensor package 100 includes a current rail 110, a soft magnetic core 120 and a packaged magnetic sensor 130. In a final assembly step these elements are encapsulated in an encapsulation 150 to form the current sensor package 100. As shown in FIG. 2. The soft magnetic core 120 of the current sensor package 100 is typically made from a metal such as iron or nickel.

Electrical current and moving electrical charges produce a magnetic field orthogonal to the current flow. The magnetic field can be described with magnetic field lines forming a cylinder around a current flow.

In one embodiment the soft magnetic magnet comprises a soft magnetic composite material. In one embodiment the soft magnetic composite material comprises an insulating material or a polymer. In one embodiment the soft magnetic composite material comprises a soft magnetic magnet material embedded in the insulating material or the polymer. In one embodiment the soft magnetic composite material comprises nickel (Ni), iron (Fe), iron-nickel (FeNi), iron-silicon (FeSi), iron-silicon-boron (FeSiB) or iron-cobalt (FeCo) particles embedded in the insulating material or polymer.

In one embodiment the soft magnetic magnet may be formed in and/or over an encapsulation of a sensor and a conductive line. In one embodiment the soft magnetic magnet may be formed in a mold. In one embodiment the soft magnetic magnet may be injected in a mold. In one embodiment the soft magnetic magnet may comprise a triangle shaped structure or a rectangular shaped structure in, on and/or around the encapsulation. In one embodiment the soft magnetic magnet may form complex two and three dimensional structures in and/or over the encapsulation.

In one embodiment the soft magnetic magnet channels or concentrates the magnetic field lines. In one embodiment the soft magnetic magnet focuses the magnetic to a specific focus point. In one embodiment the magnetic field lines are focused on a sensor chip. In one embodiment the magnetic field lines are focused on an active area of a sensor chip.

Figure 3:
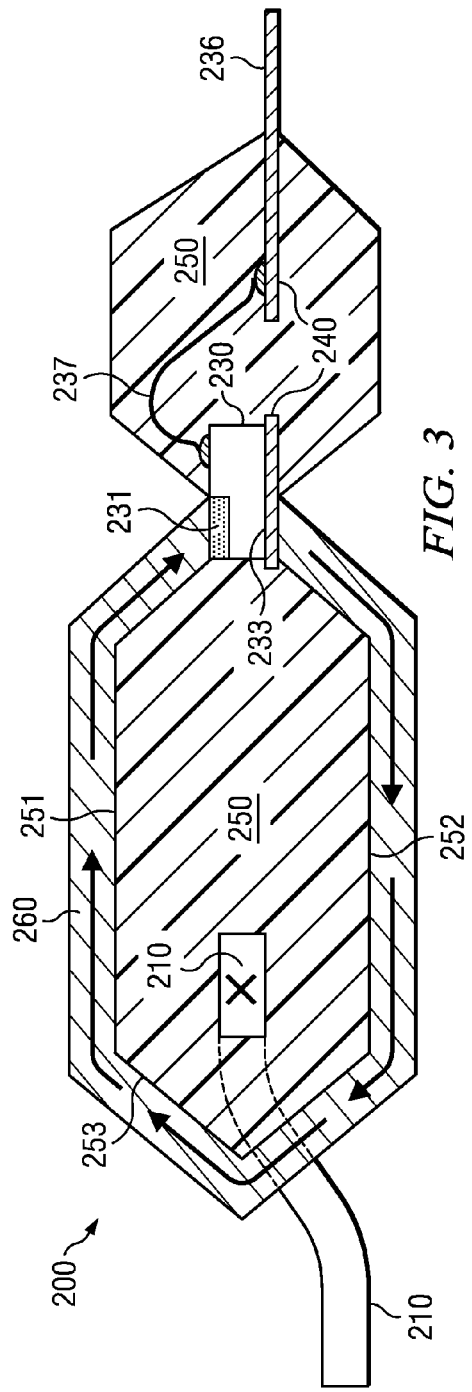
FIG. 3 shows a cross-sectional view of an embodiment of a sensor package.
Figure 4:
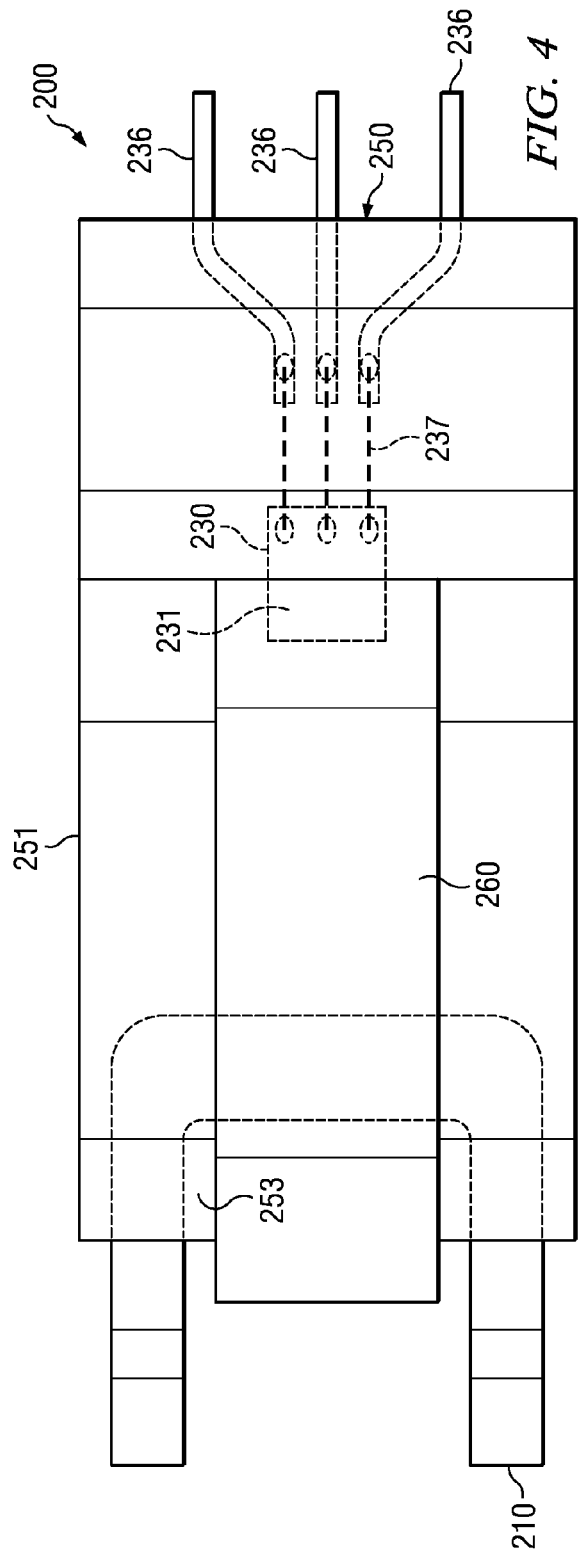
FIG. 4 shows a top view of an embodiment of a sensor package.

FIGS. 3 and 4 show an embodiment of a sensor package 200. A sensor 230 is arranged on a leadframe 240. The sensor 230 may be arranged on a sensor attach area 233 of the leadframe 240 by an adhesive, such as an epoxy. Alternatively the adhesive may be an acrylic, a silicone, an isocyanate or an other glue. After fixing the sensor 230 on the sensor attach area 233 of the leadframe 240, the sensor 230 maybe wire bonded with bond wires 237 to leads 236 of the leadframe 240. In one example the leadframe 240 may comprise three or four leads 236. Alternatively, the leadframe 240 may comprise a different number of leads 236.

FIGS. 3 and 4 further show a conductive line 210 arranged near or in the vicinity of the sensor 230. The conductive line 210 may be arranged in a sensing distance from the sensor 230. The conductive line 210 may be isolated from the sensor 230. In one embodiment the conductive line 210 may be isolated for voltages up to about 100 kV. In one embodiment the conductive 210 may be isolated for voltages up to about 10 kV. In one embodiment the conductive line 210 may be isolated for voltages up to about 1 kV.

In one embodiment the conductive line 210 is a metal such as copper (Cu) or aluminum (Al). In one embodiment the conductive line 210 is any suitable conductive material such as doped polysilicon or polysilicon.

In one embodiment the conductive line 210 is U-shaped. In one embodiment the conductive line 210 is O-shaped. In one embodiment the conductive line 210 is almost O-shaped, i.e., has a small opening at one side of an O ring. In one embodiment, the conductive line 210 is almost elliptic shaped. In one embodiment the conductive line 210 is a straight line.

In one embodiment the sensor 230 may be a magnetic sensor. The magnetic sensor 230 may measure magnetic fields produced by a current flowing through the conductive line 210. The magnetic sensor 230 generally does not interrupt the current flow in the conductive line 210. The output voltage of the magnetic sensor 230 may vary in response to changes in the current flow and therefore the related magnetic field.

In one embodiment the magnetic sensor 230 is a Hall sensor. The Hall sensor measures changes in a magnetic field. Changes in the magnetic field are measured by measuring a Hall voltage. The Hall voltage is generated transversally to a constant current flowing though a Hall plate and perpendicular to the magnetic field to be measured.

In one embodiment the magnetic sensor 230 is an anisotropic magneto resistance (AMR) sensor. AMR resistors may be made of a permalloy thin film deposited on a silicon wafer. The resistance of the film may change by 2%-3% in the presence of a magnetic field. In a typical configuration, four of these AMR resistors are connected in a Wheatstone bridge to permit measurement of a magnitude of a magnetic field.

An external magnetic field applied normal to the side of the permalloy film causes the resistance value to vary and to produce a voltage output change in the Wheatstone bridge. This change in the resistance is termed the magnetoresistive effect and is directly related to the angle of the current flow through the bridge and the magnetization vector of the film which is influenced by the magnetic field to be measured.

In one embodiment the magnetic sensor 230 is a giant magneto resistance (GMR) sensor. GMR resistors may be made of a spin valve layer stack deposited on a silicon wafer. The spin valve layer stack may comprise a conductive non-magnetic interlayer sandwiched between two magnetic layers having opposite magnetizations. The GMR resistor changes its resistance when subjected to an external magnetic field.

In a typical configuration, four of these GMR resistors may be connected in a Wheatstone bridge and two of the Wheatstone bridges may form the GMR sensor. Each half bridge of the Wheatstone bridge my comprise resistors with opposite reference magnetization. Two half bridges may form a Wheatstone bridge so that the resistors with similarly oriented reference magnetizations lie diagonally in the full bridge. The resistors of the first Wheatstone bridge and the resistors of the second Wheatstone bridge are rotated by 90 degrees.

In one embodiment the conductive line 210, the sensor 230 and the leadframe 240 are at least partially encapsulated in an encapsulation 250 with an encapsulation material or an encapsulation compound. In one embodiment the encapsulation material may comprise an insulating material. In one embodiment the encapsulation material may comprise a non-conductive material. In one embodiment the encapsulation material may comprise a dielectric material. In one embodiment the encapsulation material may comprise a polymer. In one embodiment the polymer may comprise a thermoset or a thermoplastic. In one embodiment the encapsulation 250 is formed in a mold. In one embodiment the encapsulation 250 is formed by injecting an encapsulation compound or material into a mold to form the encapsulation 250.

A thermoset is a polymer material that irreversibly cures when heated, when processed through a chemical reaction, or when processed by an irradiation. Some thermoset materials may be liquid, malleable, or even solids prior to curing and designed to be molded into their final form.

The curing process transforms the resin into a plastic or rubber by a cross-linking process. Energy and/or catalysts are added that cause the molecular chains to react at chemically active sites linking the molecular chains together into a rigid structure. The cross-linking process forms a molecule with a larger molecular weight and which is a solid material. In one embodiment curing may be achieved through heating the thermoset in a range of about 50° C. to about 250° C. In one embodiment curing may be achieved through heating the thermoset in a range of about 100° C. to about 200° C. In one embodiment curing may be achieved through heating the thermoset above a temperature of about 100° C.

A thermoplastic is a polymer that turns to a liquid when heated and freezes when cooled sufficiently. Most thermoplastics are high-molecular-weight polymers whose chains associate through weak Van der Waals forces and/or stronger dipole-dipole interactions. Thermoplastic polymers differ from thermosetting polymers in that they can be remelted and remolded. The thermoset material may comprise Cresol Novolak compounds, epoxy compounds, Furan compounds, Isocyanates, Alkyd compounds, Melamin Formaldehyde compounds or combinations thereof.

Thermoplastics are elastic and flexible above a glass transition temperature $T_g$. The transition temperature $T_g$ is a midpoint of a temperature range rather than an exactly defined temperature. Below a second, higher melting temperature, $T_m$, also the midpoint of a range, some thermoplastics have crystalline regions alternating with amorphous regions. Above $T_m$ all crystalline structure disappears and the chains become randomly inter-dispersed. In some embodiments thermoplastics have only amorphous regions below $T_m$.

A thermoplastic may comprise polyamide or polyethylene. Alternatively, a thermoplastic may comprise polyphenylene-sulfide, poly-vinyl compounds, polyoxymethylene compounds or combinations thereof.

In one embodiment the thermoplastic may be heated to a temperature of about 230° C. to about 370° C. In one embodiment the thermoplastic may be heated to a temperature of about 270° C. to about 330° C. In one embodiment the thermoplastic may be heated to a temperature of about 300° C.

A soft magnet or a soft magnetic core 260 may be formed on, in or around the encapsulation 250. Unlike a hard magnetic core, a soft magnetic core does not remain magnetized when a magnetic field is removed. A soft magnetic core may be used in applications where the magnetic field repeatedly switches or changes.

In one embodiment the soft magnet 260 may comprise soft magnetic composite material such as an insulating material or a non-conductive material plus a material with soft magnetic characteristics or properties. In one embodiment the soft magnet 260 comprises a material with soft magnetic properties embedded in the insulating material. In one embodiment the soft magnet 260 comprises an insulating material filled with soft magnetic particles. In one embodiment the soft magnet 260 comprises at least two different materials with soft magnetic properties embedded in the insulating material.

In one embodiment the insulating material is a polymer. In one embodiment the polymer may comprise a thermoset or a thermoplastic material.

In one embodiment the materials with soft magnetic characteristics or properties may comprise nickel (Ni), iron (Fe), iron-nickel (FeNi), iron-silicon (FeSi), iron-silicon-boron (FeSiB) or iron-cobalt (FeCo), for example. Alternatively, the materials may be other materials with soft magnetic properties.

In one embodiment the soft magnet 260 may be formed by depositing one layer of a soft magnetic composite material on, in and/or around the encapsulation 250.

In one embodiment the soft magnet 260 may be formed by depositing several layers of soft magnetic composite material on top of one another. In one embodiment a first layer of soft magnetic composite material may be deposited over the encapsulation 250 having a first form. Then a second layer of soft magnetic composite material may be deposited over the encapsulation 250 and the deposited first layer having a second form. Then a third layer of soft magnetic composite material may be deposited over the encapsulation 250 and the deposited first and second layer having a third form. In one embodiment the multilayer soft magnet 260 may comprise n layers all having different forms or all having the same form. Alternatively, the multilayer soft magnet 260 may comprise some layers having the same form and other layers having different forms. Complex two or three dimensional forms of the soft magnet 260 may be formed by applying such a deposition process.

In one embodiment the multi layered soft magnet 260 may comprise a first layer comprising a first soft magnetic composite material and a second layer comprising a second soft magnetic composite material. For example, the first soft magnetic composite material may be a thermoplastic material with iron (Fe) embedded therein and the second soft magnetic composite material may be a thermoset with iron-nickel (Fe—Ni) embedded therein.

In one embodiment, the soft magnet 260 may be formed by placing the encapsulation 250 in a mold and injecting the soft magnetic composite material therein. The soft magnetic composite material may be injected at a temperature of about 100° C. to about 450° C. A preferred range may be between 200° C. and 400° C. Thereafter, the mold is cooled and the soft magnetic composite material assumes the form of the mold forming the soft magnet 260.

In one embodiment, the current sensor 200 may be formed in a two step injection process. In a first step, the conductive line 210, the sensor 230, and the leadframe 240 are placed in a first mold. An insulating or a non-conductive material is injected into the mold and the encapsulation 250 is formed. Then, in a second step, the encapsulation 250 is placed in a second mold. A soft magnetic composite material is injected in the mold to form the soft magnet 260 in, on or around the encapsulation 250. The first mold may comprise a different form than the second mold.

FIGS. 3 and 4 show an embodiment of an arrangement of the soft magnet 260 on the encapsulation 250. The soft magnet overlies an upper surface 251 of the encapsulation 250, a lower surface 252 of the encapsulation 250 and a sidewall 253 of the encapsulation 250. The soft magnet 260 is arranged in a rectangular form and overlies the active area 231 of the sensor 230.

Figure 5:
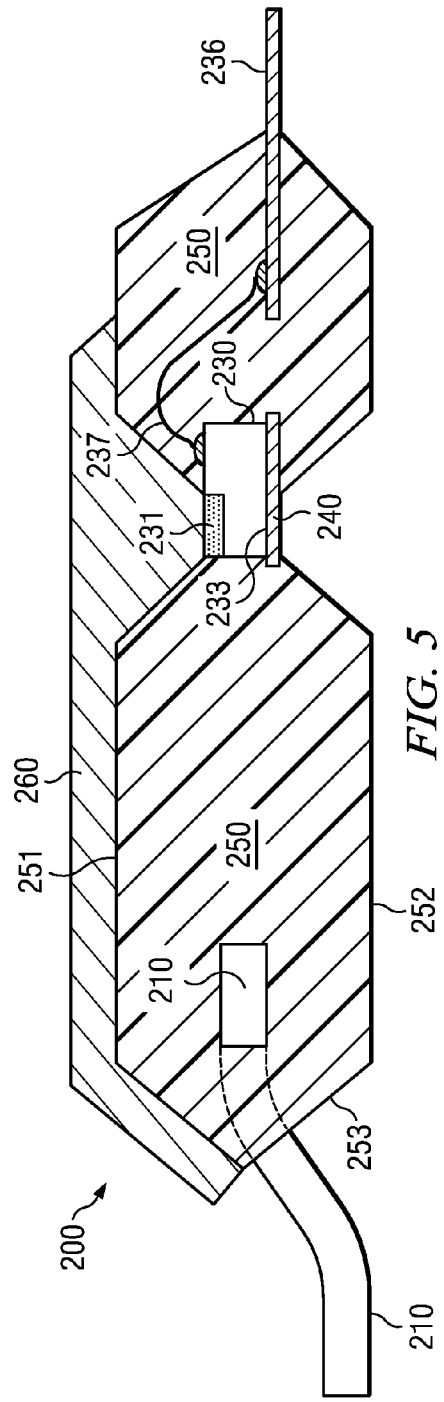
FIG. 5 shows a cross-sectional view of an embodiment of a sensor package.

FIG. 5 shows another embodiment of an arrangement of the soft magnet 260 on the encapsulation 250. The soft magnet 260 is arranged on the upper surface 251 of the encapsulation 250 and on parts of the sidewall 253 but not on the lower surface 252. The soft magnet 260 covers the sensor 230 completely and not only the active area 231 of the sensor 230.

Figure 6:
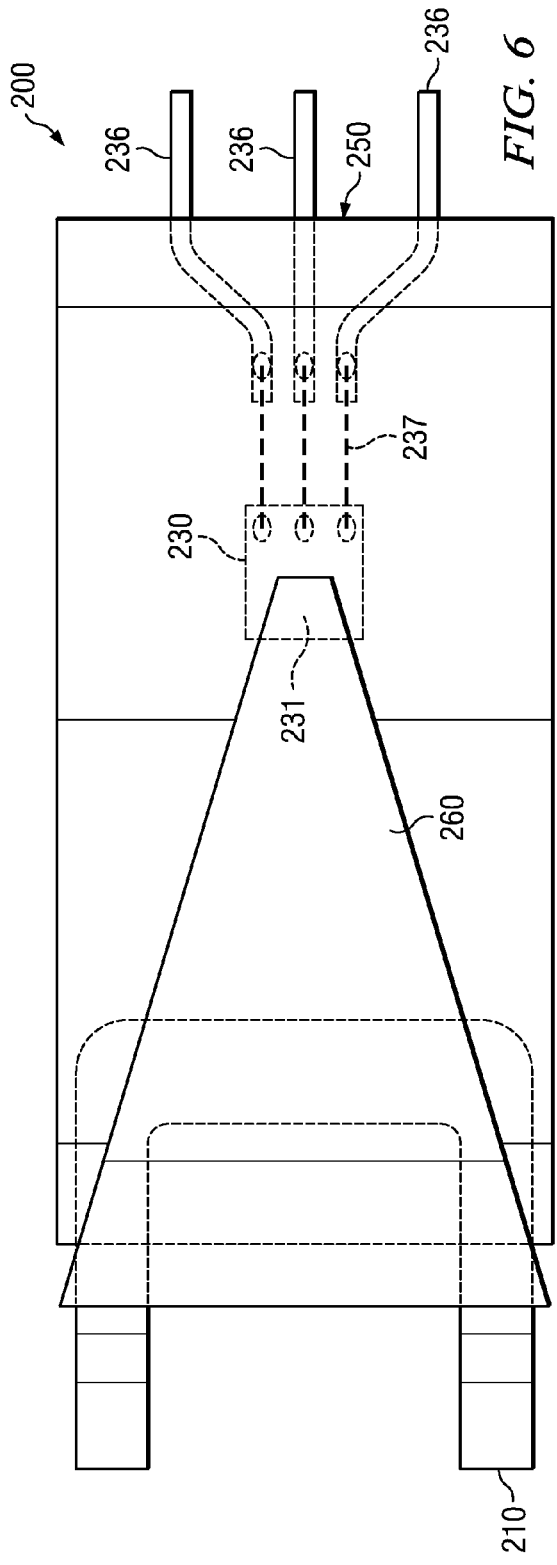
FIG. 6 shows a top view of an embodiment of a sensor package.

FIG. 6 shows yet another embodiment of an arrangement of the soft magnet 260 on the encapsulation 250. The soft magnet 260 forms a triangle wherein one angle of the triangle overlies the active area 231 of the sensor 230. An advantage of such an arrangement is that the magnetic field lines may be channeled or concentrated on the active area 231 of the sensor 230. A further advantage is that the magnetic field lines may be focused on the active area 231 of the sensor 230.

Figure 7:
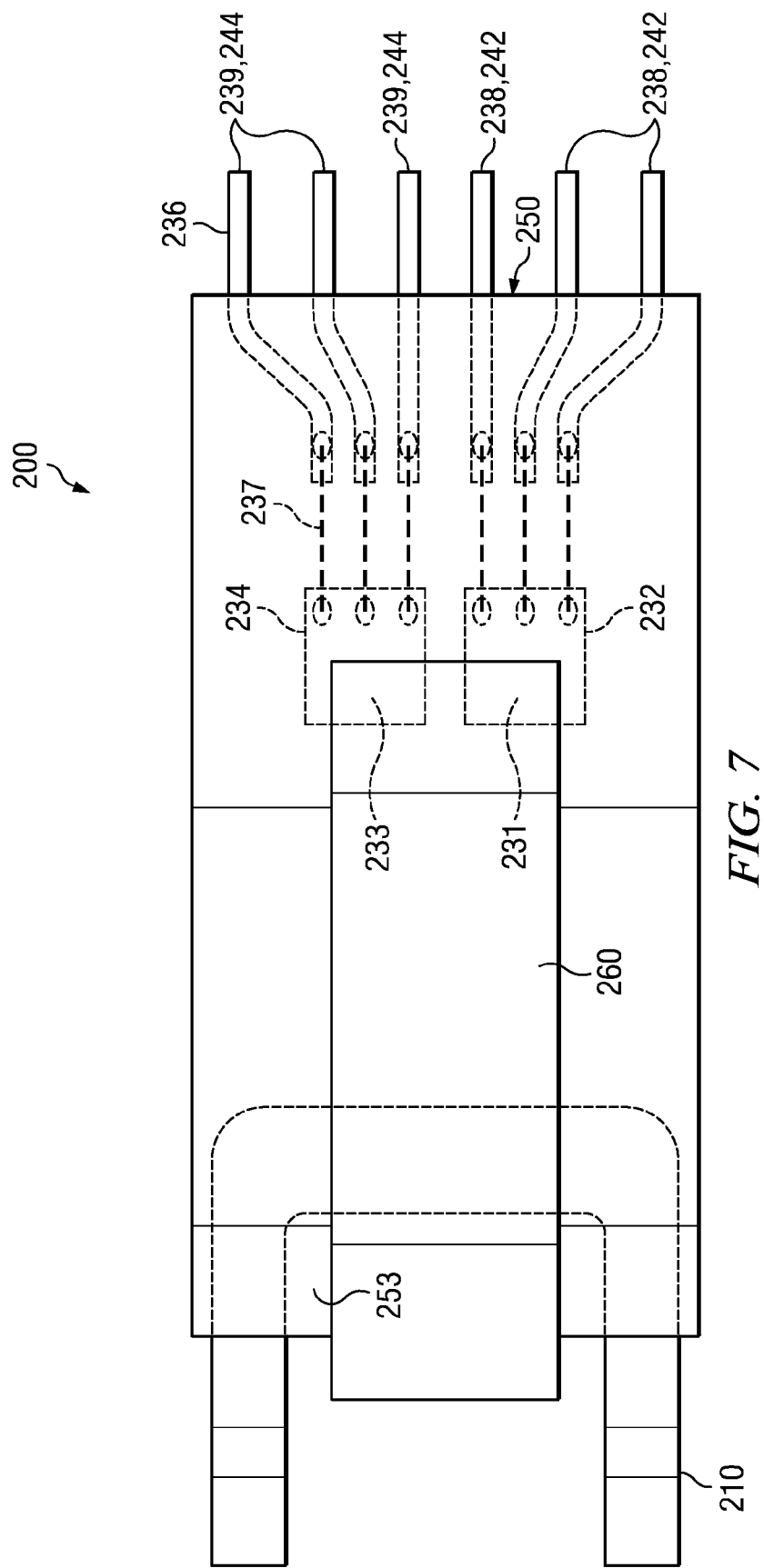
FIG. 7 shows a top view of an embodiment of a sensor package comprising two sensors.

FIG. 7 shows an embodiment with two or more sensors. FIG. 7 shows a first sensor 232 arranged on a first leadframe 242 and a second sensor 234 arranged on a second leadframe 244. The first leadframe 242 comprises first leads 238 and the second leadframe 244 comprises second leads 239. The first sensor 232 comprises a first active area 231 and the second sensor 234 comprises a second active area 233. The first and second sensors 232, 234, the first and second leadframes 242, 244 and the conductive line 210 are at least partially embedded in an encapsulation 250. The soft magnet 260 overlies the encapsulation 250 and overlies at least the first and second active areas 231, 233 of the first and second sensors 232, 234. In one embodiment the first and second sensors 232, 234 are the same type of sensor. In one embodiment the first and second sensors 232, 234 may comprise different types of sensors. For example, sensor 232 may be a Hall sensor and sensor 234 may be an AMR sensor.

Figure 8:
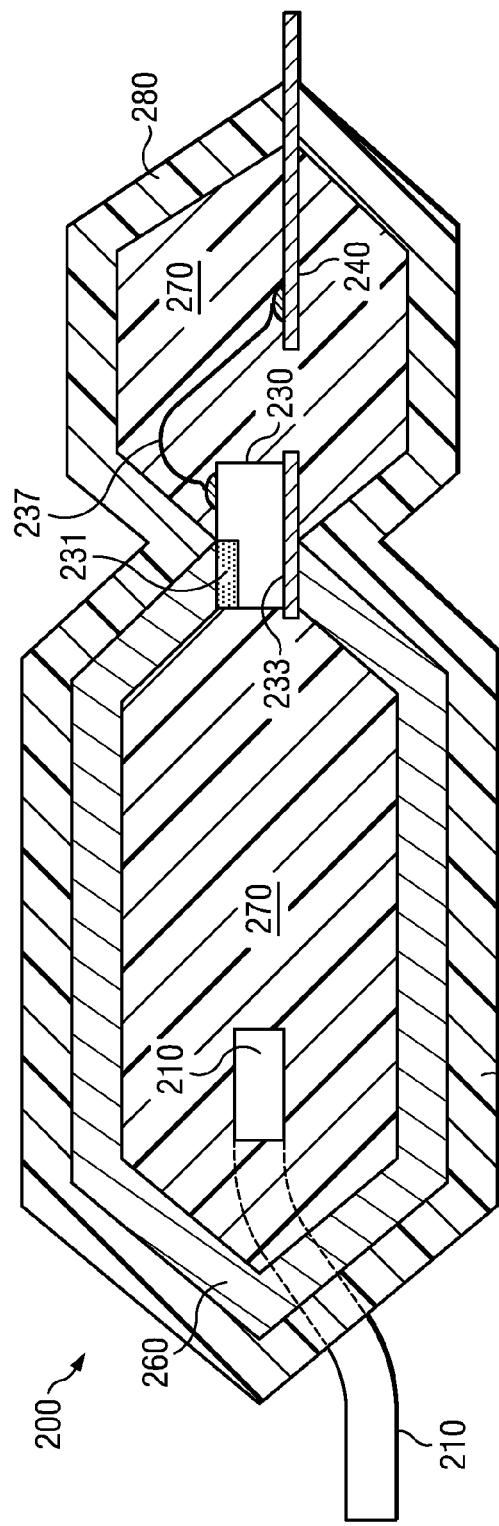
FIG. 8 shows a cross-sectional view of an embodiment of a sensor package.

FIG. 8 shows an embodiment of an arrangement of the soft magnet 260 embedded in an encapsulation. In one embodiment an inner encapsulation 270 is formed by at least encapsulating the conductive line 210, the sensor 230 and the leadframe 240. A soft magnet 260 is formed over the surface of inner encapsulation 270. The soft magnet 260 is formed according to one of the previously disclosed embodiments. Finally, an outer encapsulation 280 is formed encapsulating the inner encapsulation 270 and the soft magnet 260. In one embodiment the outer encapsulation 280 may only partially encapsulate the inner encapsulation 270 and/or the soft magnet 260. In one embodiment the outer encapsulation 280 may comprise the same material as the inner encapsulation 270. In another embodiment the outer encapsulation 280 may comprise a different material than the inner encapsulation 270.

While arrangement of the soft magnet 260 has been described with reference to illustrative embodiments, this description is not intended to be construed in a limiting sense. A person skilled in the art will acknowledge various modifications and combinations of the illustrative embodiments. For example, the soft magnet 260 may be arranged partially in the encapsulation 250 and partially outside the encapsulation 250 or the soft magnet 260 may be embedded in the encapsulation 250 having a surface not covered by the encapsulation 250.

Figure 9:
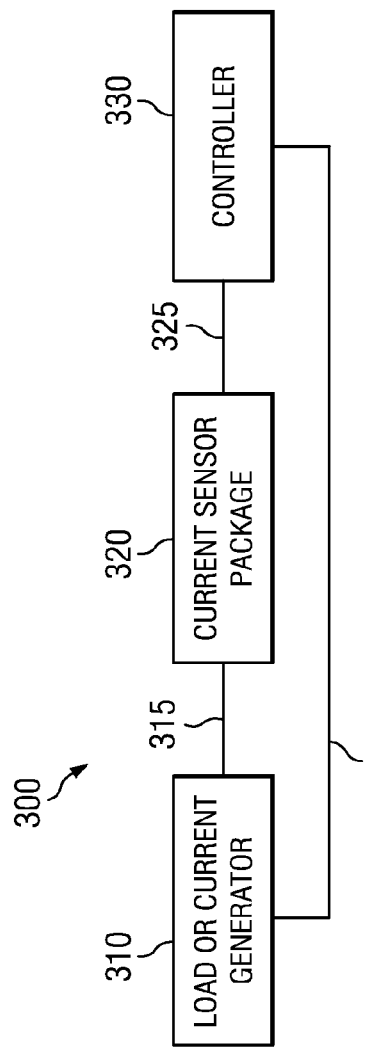
FIG. 9 shows an application of a sensor package.

FIG. 9 shows an application of a current sensor package 320 in a system 300. FIG. 9 shows a load or a current generator 310 connected to a sensor package 320. The load or the current generator 310 is electrically connected via line 315 to the conductive line of the sensor package 320. The leads of the sensor package are electrically connected via line 325 to a controller 330 and the controller 330 is electrically connected via line 335 to the current generator or load 310.

The load or the current generator 310 may be a chargeable or non-chargeable battery. In one embodiment the load or current generator 310 is a power generator such as a solar cell, a fuel cell or an electromagnetic dynamo. In one embodiment the load or current generator 310 is a power supply for a building. In one embodiment the load or current generator 310 is a security system for a building wherein the current sensor package may recognize an interruption in the current if someone brakes into the building by an unauthorized opening of a door or a window. The current sensor package 320 may be one of the previously disclosed current sensor packages. The controller 330 may be a microcontroller or a microprocessor.

In one embodiment the current sensor package 320 measures the current generated by the current generator 310 and forwards the results or the information via line 325 to the controller 330. The controller 330 reviews the information received from the current sensor package 320 and instructs the current generator 310 via line 335 to increase or to decrease current generation. In some embodiments the controller 330, based on received information from the current sensor package 320, may shut down the current generator 310 when specification limits are met or violated.

In one embodiment the current sensor package 320 measures the current coming from the load 310 and forwards the results or the information via line 325 to the controller 330. The controller 330 reviews the information received from the current sensor package 320 and sends signals via line 335 to adjust the electrical behavior of the load 310. In some embodiments the controller 330, based on received information from the current sensor package 320, may shut down the load when specification limits are met or violated.

The system 300 can be used in many different applications. For example, the system 300 may be used in electro vehicles, security systems, local power generation systems or in buildings. In one embodiment these systems may comprise embodiments of the sensor package 200. In one embodiment these systems may comprise several or a plurality of embodiments of the sensor package 200.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A sensor package comprising:
a conductive line configured to carry a current;
a sensor arranged proximate to the conductive line, the sensor configured to measure the current;
an encapsulation material separating the conductive line from the sensor, the encapsulation material at least partially encapsulating the conductive line and at least partially encapsulating the sensor; and
a soft magnetic material at least partially arranged on or around the encapsulation material, wherein the soft magnetic material is disposed on the sensor.

2. The sensor package according to claim 1, wherein the soft magnetic material comprises soft magnetic particles embedded in a polymer.

3. The sensor package according to claim 2, wherein the polymer is a thermoset material or a thermoplastic material.

4. The sensor package according to claim 1, wherein the sensor is a magnetic sensor.

5. The sensor package according to claim 4, wherein the magnetic sensor is a Hall sensor, an AMR sensor, or a GMR sensor.

6. The sensor package according to claim 1, wherein the conductive line comprises a U shaped conductive line, an O shaped conductive line, an almost O shaped conductive line, an almost elliptic shaped conductive line, or a straight conductive line.

7. The sensor package according to claim 1, wherein the soft magnetic material is arranged over an active area of the sensor, and wherein no encapsulation material is located between the active area of the sensor and the soft magnetic material.

8. The sensor package according to claim 1, wherein the soft magnetic material is arranged on or around the encapsulation material such that the soft magnetic material is configured to channel magnetic field lines to a focus point of the sensor.

9. The sensor package according to claim 1, wherein the soft magnetic material is directly disposed on the sensor.

10. The sensor package according to claim 9, wherein the soft magnetic material is directly disposed only on an active area of the sensor.

11. The sensor package according to claim 1, further comprising a leadframe and a plurality of leads, wherein the sensor is disposed on the leadframe and electrically connected to the plurality of leads.

12. A system comprising:
a current generator;
the sensor package according to claim 1, wherein the sensor of the sensor package is configured to measure the current of the conductive line; and
a controller electrically connected to the sensor and the current generator, wherein the controller is configured to instruct the current generator to increase or decrease the current.

13. The sensor package according to claim 1, further comprising leads, wherein the sensor electrically connected to the leads, wherein the leads are disposed in a first portion of the encapsulation material, wherein the conductive line is disposed in a second portion of the encapsulation material, and wherein the soft magnetic material is disposed only on the second portion.

14. The sensor package according to claim 1, wherein the sensor is a sensor chip and wherein the soft magnetic material is disposed directly on the sensor chip.

15. A sensor package comprising:
a sensor comprising an active area and configured to measure a current, the sensor disposed on a leadframe;
a conductive line configured to carry the current, the conductive line disposed in a vicinity to the sensor;
a first encapsulation material partially encapsulating the conductive line and the sensor;
leads electrically connected to the sensor;
a second encapsulation material partially encapsulating the sensor and the leads; and
a soft magnetic material directly disposed on at least a portion of the first encapsulation material and the active area, wherein the soft magnetic material is not disposed on the second encapsulation material.

16. The sensor package according to claim 15, wherein the soft magnetic material is directly disposed on a portion of the leadframe.

17. The sensor package according to claim 15, wherein the first encapsulation material and the second encapsulation material are the same.

18. The sensor package according to claim 15, wherein the soft magnetic material is only disposed on the first encapsulation material.

19. The sensor package according to claim 15, wherein the first encapsulation material comprises a first polymer and the second encapsulation material comprises a second polymer.

20. The sensor package according to claim 15, wherein the sensor is a sensor chip.

21. A sensor package comprising:
a sensor comprising an active area and configured to measure a current, the sensor disposed on a leadframe;
a conductive line configured to carry the current, the conductive line disposed in a vicinity to the sensor;
leads electrically connected to the sensor;
a first encapsulation material partially encapsulating the conductive line, the sensor and the leads, the first encapsulation material exposing at least a portion of the sensor active area of the sensor; and
a soft magnetic material at least partially disposed directly on the first encapsulation material and the active area, wherein the leads are disposed in a first portion of the first encapsulation material, wherein the conductive line is disposed in a second portion of the first encapsulation material, wherein the first portion and the second portion of the first encapsulation material are separated by the sensor, and wherein the soft magnetic material is disposed on the second portion of the first encapsulation material but not on the first portion of the first encapsulation material.

22. The sensor package according to claim 21, wherein a second encapsulation material is disposed on the first encapsulation material and the soft magnetic material.

23. The sensor package according to claim 22, wherein the second encapsulation material is different than the first encapsulation material.

24. A sensor package comprising:
a conductive line configured to carry a current;
a sensor arranged proximate to the conductive line, wherein the sensor is configured to measure the current;
an encapsulation material separating the conductive line from the sensor and at least partially encapsulating the conductive line and the sensor, wherein the sensor comprises an encapsulation material free area;
a soft magnetic material arranged on or around the encapsulation material, wherein the soft magnetic material is disposed on the encapsulation material free area of the sensor; and
leads electrically connected to the leads, wherein the leads are disposed in a first portion of the encapsulation material, wherein the conductive line is disposed in a second portion of the encapsulation material, and wherein the soft magnetic material is disposed only on the second portion.

* * * * *

UNITED STATES PATENT AND TRADEMARK OFFICE
CERTIFICATE OF CORRECTION

| | | |
|---|---|---|
| PATENT NO. | : 9,121,885 B2 | Page 1 of 1 |
| APPLICATION NO. | : 12/857242 | |
| DATED | : September 1, 2015 | |
| INVENTOR(S) | : Klaus Elian | |

It is certified that error appears in the above-identified patent and that said Letters Patent is hereby corrected as shown below:

Claims
In Col. 9, line 20, claim 21, delete "sensor".

Signed and Sealed this
Ninth Day of February, 2016

Michelle K. Lee
*Director of the United States Patent and Trademark Office*